United States Patent [19]

Gubitosa et al.

[11] Patent Number: 4,522,931

[45] Date of Patent: Jun. 11, 1985

[54] METHOD FOR THE PREPARATION OF SUPPORTED CATALYSTS AND SUPPORTED CATALYSTS THUS OBTAINED

[75] Inventors: Giuseppe Gubitosa; Antonio Berton; Nicola Pernicone, all of Novara; Graziano Vidotto, Padua, all of Italy

[73] Assignee: Montepolimeri S.p.A, Milan, Italy

[21] Appl. No.: 530,755

[22] Filed: Sep. 9, 1983

[30] Foreign Application Priority Data

Sep. 10, 1982 [IT] Italy .................. 23197 A/82

[51] Int. Cl.³ .................. B01J 21/18; B01J 31/02
[52] U.S. Cl. .................. 502/150; 502/185; 564/423
[58] Field of Search .............. 502/185, 184, 183, 182, 502/334, 339, 506, 300, 150, 151

[56] References Cited

U.S. PATENT DOCUMENTS

| | | | |
|---|---|---|---|
| 1,088,673 | 2/1914 | Ellis | 502/300 |
| 2,285,277 | 6/1942 | Henke et al. | 502/185 |
| 2,823,235 | 2/1958 | Lindamere et al. | 502/174 |
| 2,930,765 | 3/1960 | Cooper et al. | 502/185 |
| 2,930,766 | 3/1960 | Lacey | 502/185 |
| 3,736,266 | 5/1973 | Shrage | 502/182 |
| 4,136,059 | 1/1979 | Jalan et al. | 502/101 |
| 4,239,653 | 12/1980 | Bodnar et al. | 502/185 |
| 4,367,167 | 1/1983 | Lee | 502/339 |

Primary Examiner—P. E. Konopka

[57] ABSTRACT

A method for the preparation of catalysts, particularly suitable for the hydrogenation of organic compounds, according to which method a catalytic element, preferably selected from the VIII Group elements, is supported on the outer surface of an adsorbent carbon, said method being characterized by the fact that:

(a) said carbon containing an amount of ash lower than 1% by weight, is suspended in water;

(b) a liquid immiscible with water is added to the suspension obtained according to (a), the volume of said immiscible liquid being substantially equal to or lower than the volume of the carrier's pores;

(c) an aqueous solution, containing a compound of the catalytic element, is brought into contact with the suspension obtained according to (b).

7 Claims, No Drawings

METHOD FOR THE PREPARATION OF SUPPORTED CATALYSTS AND SUPPORTED CATALYSTS THUS OBTAINED

BACKGROUND OF THE INVENTION

In general, the amount of supported component (in particular noble metals of Group VIII) is the smallest possible, provided that, the other conditions remaining the same, the same results or better results are obtained than those obtained when greater quantities of catalytic component are used. In other words, the aim is that of raising the ratio "carrier/catalytic compound" to a maximum. When the catalyst is used, for instance, in the form of a powder dispersed in a liquid reaction medium, the waste of catalytic component in some instances may be considerable, because of the more or less partial solubility of the component in the reaction liquid, as well as because of the loss during the separation of the catalyst from the end product, for instance by filtering or by centrifuging.

OBJECT OF THE INVENTION

One object of the invention is that of increasing the (carrier/catalytic compound) ratio, while maintaining the parity of the results; other objects still, will appear even more evident from the following description.

DESCRIPTION OF THE INVENTION

In its more general form, the invention concerns a method for the preparation of catalysts, particularly suitable for the hydrogenation of organic compounds, according to which method a catalytic element, preferably selected from the VIII Group elements and especially from the group comprising Ni, Pd, Rh and Pt, is supported on the outer surface of an adsorbent carbon, said method being characterized by the fact that:

(a) said carbon, containing an amount of ash lower than 1, and preferably 0.6% by weight, is suspended in water;

(b) a liquid, immiscible with water, preferably selected from the group comprising n-hexane, n-heptane, benzene and toluene, is added to the suspension obtained according to (a), the volume of said immiscible liquid being substantially equal to or lower than the volume of the carrier's pores;

(c) an aqueous solution, containing a compound of the catalytic element, is brought into contact with the suspension obtained according to (a) and (b).

There are quite a number of possible forms of embodiment of the present invention. Thus, according to one particularly convenient form, an activated carbon of a low content of ash (that is, containing less than 1%, but preferably less than 0.6% by weight in ash) is suspended in $H_2O$ and is then treated with an aqueous solution of compounds of metals of Group VIII (in such amount as to have at the end from 0.1% to 5% by weight of supported metal), the carbon having been previously put into contact with a solvent immiscible with water, said solvent being present in amounts equal to or smaller than the volume of the pores of the activated carbon.

After the addition of the solvent and before adding the aqueous solution of the catalytic compound, it is advisable to add also the aqueous solution of an alkaline compound, in such amount as to reach a pH value (within the suspension) between 7 and 8.5; the same pH, after the addition of the catalytic compound, must then be brought up to a level equal to or greater than 12.

The preliminary filling of the pores, in particular those having smallest diameter, with the water-immiscible solvent, hinders the introduction into the inside of the pores of the metal compound which will thus deposit on the outer layer of the granules of the support. If there is a treatment for the conversion of such a compound into metal, a catalyst is obtained in which the metal particles are concentrated preferably in said outside layer, in this way more easily accessible for the reactant molecules, thereby avoiding phenomena of diffusion of reactants and products inside of the porous structure of the catalyst granules, which reactants and products would considerably reduce the catalyst's performance. The present invention may also involve considerable improvements in the selectivity, just thanks to the reduction of the mentioned internal diffusion phenomena.

Particularly good results are obtained in the case of Pd-based catalysts (on carbon) used for the hydrogenation of organic nitro-, nitrous or nitrilo-organic derivatives, and more particularly of dinitrotoluene (DNT) to toluenediamine (TDA); in this case the simultaneous impregnation of the carbon, treated with an organic solvent, with the aqueous solution of a Pd-compound and of an inorganic base, leads to the formation of more active catalysts, in comparison with those of the prior art. During the impregnation (or soaking), the noble metal is deposited on the activated carbon substantially in the form of an extremely dispersed oxide, in concentrations from 0.5% to 5% by weight of Pd. More particularly, the catalysts, in a concentration of 2.5% by weight of Pd, prepared according to the present process, exert a catalytic activity, expressed as moles of converted organic compound/h/gram of metal (for instance, in the hydrogenation of a mixture of 20% of 2,6-dinitrotoluene and 80% of 2,4-dinitrotoluene to the corresponding amines), approximately double with respect to a usual commercial catalyst at 5% of Pd, all the other operating conditions remaining the same. The percentage of ash is determined by weighing the residue of the calcining in a muffle furnace (e.g. at 700° C. for at least 4 hours).

The precursor of the active component of the catalyst may be a water-soluble Pd-compound, preferably $H_2PdCl_4$, obtained from $PdCl_2$ and from a stoichiometric quantity of HCl. The inorganic base may be a hydroxide of alkaline elements, preferably KOH. The carbon must have a great surface area, between 600 and 1500 $m^2/g$, with a mean pore diameter of 2.5 nm (25 Å) and an apparent density from 0.3 to 0.8 $g/cm^3$. The catalyst may be dried before its use but may also be used as such, with considerable contents of liquid (up to more than 20% by weight), for instance when a liquid phase hydrogenation is carried out in the presence of a suspended-bed catalyst.

The examples that follow, are given for purely illustrative purposes and in no way shall be intended as a limitation of the scope of the invention.

EXAMPLE 1

The process was started from a commercial carbon produced by LURGI UMWELT u. CHEMOTECHNIK GmbH, of the type Brilonit KE, having a specific surface area of about 800 $m^2/g$; this carbon showed an ash residue, after calcining in a muffle at 700° C. for at least 4 hours, of about 5% by weight. This carbon was then subjected to a purification process with diluted $HNO_3$, according to the method indicated further on. 640 g of the commercial carbon were thereupon suspended in 2.5 lt of a 10% by weight solution of $HNO_3$ and the ensuing suspension was then maintained under stirring and heated at 80° C. for 4 hours. The carbon was then filtered and repeatedly washed with distilled water (until the filtrate had a pH from 4 to 5) and was not dried before use. 10 grams of the activated carbon thus obtained, having a very low ash content (0.5% by weight), were suspended in 60 cm$^3$ of $H_2O$; the pH of the suspension was 3.05. To this suspension were thereupon admixed, under constant stirring, 5 cm$^3$ of n-heptane, (in the course of 2 h). The pH was stabilized on the value 2.1. Thereafter, the pH was brought up to 8 by the addition of 2.6 cm$^3$ of a 0.42M KOH solution. The suspension, within about 1 hour, had added thereto 33 cm$^3$ of a $H_2PdCl_4$ solution formed from 0.41 g of $PdCl_2$ and $4.7\times10^{-3}$ moles of HCl, while maintaining the pH between 7.5 and 8, by the continuous addition of said KOH solution. At the end of the impregnation, the pH was brought up to 12 by further addition of KOH and the suspension was then kept under constant stirring overnight, at room temperature. Successively, the catalyst was filtered and washed with $H_2O$ until obtaining a neutral filtrate free from chlorides. The Pd content, determined by means of atomic absorption, was 2.3% by weight, while the chlorides content was 0.05% by weight. $60\times10^{-3}$ grams of the thus obtained catalyst were loaded into a 200 cm$^3$ glass reactor, mounted on a rocking stirrer and connected, through a vacuum-generating system, to a gas-filled burette at constant pressure (substantially atmospheric) and to a compensating funnel, reactor, burette and funnel being maintained at a thermostatically stabilized temperature of 30° C.

This system was degassed and then filled with an inert gas while the catalyst was additioned with 0.5465 g of 2.4-dinitrotoluene dissolved in 15 cm$^3$ of ethylacetate; the inert gas was then substituted with $H_2$, filling the burette with a volume of $H_2$ sufficient for the reaction, whereafter the reactor was subjected to stirring at 300 strokes/minute. After about 1 hour (the system being kept at 30° C.), the solution of DNT was added to the suspension of the catalyst, while stopping the stirring for 15 seconds; the stirring was resumed and the measuring of the wasted $H_2$ (as a function of time) was started. At the end, when no further absorption of $H_2$ took place, the hydrogenation of DNT was considered to be completed; the gas-chromatographical analysis of the reaction solution confirmed this assumption. From the $H_2$ volume it was possible to calculate the reaction rate, expressed as moles of converted DNT/hour/g Pd; the reaction rate, in the case of the catalyst prepared according to example 1, was 3.10 moles/h/g of Pd.

EXAMPLE 2

(comparative ex.)

The hydrogenation of example 1 was repeated, while using an Engelhard catalyst prepared according to conventional methods and containing 5% by weight of Pd on an activated carbon carrier, thereby attaining an operative capacity of only just 1.6 moles/h/g.

EXAMPLE 3

A 1 liter autoclave with a thermostatically stabilized temperature, fitted with a pressure gauge (manometer), a mechanical stirrer and a feeding tank of about 100 cm$^3$, connected through a vacuum-generating system to a $H_2$-containing tank, of known volume and kept at constant temperature, was loaded with an amount of the catalyst prepared according to example 1, equal to $50\times10^{-3}$ g. The system was then put under vacuum and filled with an inert gas; to the catalyst were thereupon added 200 cm$^3$ of n-octanol and the tank was then loaded with 12.75 g of DNT and 50 cm$^3$ of n-octanol. The inert gas was then replaced by $H_2$, the autoclave was loaded with $H_2$ under pressure and put into communication, through a pressure reducing valve, with the $H_2$ tank.

Both the DNT containing tank as well as the autoclave were heated approximately at 130° C. The mechanical stirring, (ca. 1200 rpm) was started during the heating phase. Once the system had stabilized at the desired temperature and pressure (ca. 130° C. and 3 atm. respectively), the DNT solution was added to the catalyst suspension. The volume of $H_2$ was measured with reference to the pressure difference in the $H_2$-tank; during the tests, both temperature and pressure were maintained rigorously constant. The conversion rate of DNT (114 moles/h/g of Pd) was determined following the same criteria of example 1 for the test at 30° C. and at atmospheric pressure.

EXAMPLE 4

(comparative)

Example 3 was repeated, while replacing the catalyst of example 1 by the commercial catalyst of example 2 (Pd=5%); the productivity dropped immediately to 57.7 moles/h/g.

EXAMPLES 5 AND 6

Activity tests were carried out within a reactor greater than that used in the previous examples, while using, as a reaction medium, a mixture containing 80% 2.4 TDA and 20% 2.6 TDA.

The feed contained 75% by weight of the reaction medium, mentioned above, and 25% by weight of a mixture containing 80% 2.4-DNT and 20% 2.6-DNT. Said feed contained, furthermore, 62 ppm of suspended catalyst. The operative conditions were: Temperature=130° C.; $H_2$ pressure=3 atm.(gauge).

The two tests were carried out using in one instance a catalyst with 2.5% of Pd, prepared according to the invention (and according to example 1) and in the other instance the catalyst with 5% Pd indicated in example 2. Reaction rates remaining the same, we obtained DNT-conversions of equal value and equal values for the selectivity to TDA, what means that the catalyst prepared according to the invention owns a double catalytic activity (moles of converted DNT/h/g) with respect to the usual catalyst with 5% Pd.

EXAMPLES 7 AND 8

(comparative ex.)

Example 1 was repeated, but for the fact that, after the impregnation with $H_2PdCl_4$, the pH of the suspension was left at the value 8; the Pd content was 2.25% by weight. The catalytic activity, at 30° C. and at atmospheric pressures, was 2.4 moles/h/g of Pd, while, at 130° C. and 3 atm, it was 103.7 moles/h/g.

EXAMPLE 9

Example 1 was repeated, but for the fact that, after having brought the pH up to 12, the suspension was heated for about 1 hour at ca. 90° C.; the Pd content was 2.38%, while the catalytic activity, at 30° C. and under atmospheric pressure, was 3.15 moles/h/g.

EXAMPLE 10

10 g of "Brilonit" carbon with a high content in ashes (5%), as indicated in example 1, were suspended, without pre-treatment with $HNO_3$, in 50 $cm^3$ of $H_2O$. To this suspension were then added, under constant stirring and at a pH from 9 to 9.5, 5 $cm^3$ of n-heptane; after the suspension pH was stabilized on the value 10, we started the dripping of the $H_2PdCl_4$ solution containing 0.25 g of Pd. When the pH of the suspension dropped to 7.5, a 0.42M KOH solution was added in such an amount that the pH of the suspension swung around the value 8. At the end of the addition of the Pd solution, the pH of the catalytic suspension was brought up to 12 by a further addition of KOH solution. The solution was then maintained under stirring overnight. Thereafter, the catalyst was filtered and washed with distilled $H_2O$ until obtaining a neutral filtrate free from chlorides. The Pd content was 2.77% by weight, while the catalyst activity, at 30° C. and under atmospheric pressure, was 1.70 moles/h/g.

EXAMPLE 11

(comparative)

10 g of the "Brilonit" carbon of example 10 were suspended in 40 $cm^3$ of distilled $H_2O$, while the pH of the suspension was stabilized on the value 3.2 by addition of diluted $HNO_3$. Successively were added 7 $cm^3$ of n-heptane, and the preparation was then carried out according to example 10. The Pd content was 3% by weight, while the catalytic activity, at 30° C. and under atmospheric pressure, was 1.72 moles/h/g.

EXAMPLE 12

79 g of a carbon with a low ash content, like the one mentioned in example 1, were suspended in 50 $cm^3$ of distilled $H_2O$, and additioned with 7 $cm^3$ of n-hexane. Once the pH of the suspension was stabilized on a value of 2.2, a 0.5M solution of KOH was added in order to bring the pH value up to 7.5. Thereafter we added a $H_2PdCl_4$ solution containing 0.25 g of Pd at constant pH (8). At the end of the impregnation with $H_2PdCl_4$, the pH was raised up to 12 by further addition of KOH. The catalyst was thereupon filtered and washed with $H_2O$ until obtaining a neutral filtrate free from chlorides. The Pd content was 2.82%, while the catalytic activity, at 30° C. and under atmospheric pressure, was 4.10 moles/h/g, while at 130° C. and under a pressure of 3 atm, it was 130 moles/h/g.

EXAMPLE 13

Example 12 was repeated, but for the fact that a smaller amount of $H_2PdCl_4$ was added, as to obtain a catalyst with 1.5% by weight of Pd; the catalytic activity, at 30° C. and under atmospheric pressure, was 1.72 moles/h/g.

EXAMPLE 14

10 g of commercial activated carbon with a low ash content, like the one mentioned in example 1, were suspended in a mixture consisting of 100 $cm^3$ of $H_2O$ and of 8.5 $cm^3$ of benzene. After the pH of the suspension was stabilized on the value 2.15, it was brought up to 7.5 by the addition of a 0.5M solution of KOH. Thereafter, a $H_2PdCl_4$ solution, containing 0.25 g of Pd, was added to the suspension, the pH being kept at 7.5–8, by continuous addition of KOH. At the end the pH was brought up to 10 by further addition of KOH. The suspension was kept under stirring overnight, and the catalyst was then filtered and washed with $H_2O$ until obtaining a neutral filtrate free from chlorides. The Pd content was 2.60% by weight, while the catalytic activity, at 30° C. and under atmospheric pressure, was 3.4 moles/h/g, while at 130° C. and under 3 atm it was 128 moles/h/g.

EXAMPLE 15

Example 14 was repeated, but for the fact that the $H_2PdCl_4$ solution contained 0.5 g of Pd. The Pd content of the catalyst was 5% by weight, while the catalytic activity, at 30° C. and under atmospheric pressure, was 2.14 moles/h/g.

EXAMPLE 16

Example 11 was repeated, except that the $H_2PdCl_4$ solution was containing 0.1 g Pd; the resulting catalyst contained 1.08% by weight of Pd with a catalytic activity, at 30° C. and under atmospheric pressure, of 2.5 moles/h/g.

What we claim is:

1. A method of preparing a catalyst for the hydrogenation of organic compounds, according to which method a catalytic element, selected from the Group VIII elements, is supported on the outer surface of an adsorbent carbon, wherein:
   (a) said carbon, containing an amount of ash lower than 1% b.w., is suspended in water;
   (b) a liquid hydrocarbon, immiscible with water, is added to the suspension obtained according to (a), the volume of said hydrocarbon being substantially equal to or lower than the volume of the pores of the adsorbent carbon carrier;
   (c) the pH of said suspension, obtained according to (b), is brought to a value between 7 and 8.5;
   (d) an aqueous solution, containing a compound of the catalytic element, is brought into contact with the suspension obtained according to (c), while keeping the pH constant within said 7–8.5 range, the pH is then raised to a value equal to or higher than 12 in accordance with known techniques; and
   (e) the solid catalyst thus obtained is recovered from the mother liquor by a known, conventional procedure.

2. A method according to claim 1, wherein said hydrocarbon is selected from the group consisting of n-hexane, n-heptane, benzene and toluene.

3. A method according to claim 1, wherein said low-ash carbon is obtained from a carbon containing a higher amount of ash by means of a treatment with an acid.

4. A method according to claim 3, wherein said acid is nitric acid.

5. A method of preparing a supported catalyst for the hydrogenation of nitro-aromatic compounds, according to which method Pd is deposited on the outer surface of a carrier consisting of an adsorbent carbon, wherein:
   (a) said carbon, containing an amount of ash lower than 0.6% b.w., is suspended in water;
   (b) a liquid hydrocarbon, immiscible with water and selected from the group consisting of n-hexane, n-heptane, benzene and toluene, is added to the suspension obtained according to (a), the volume of said hydrocarbon being substantially equal to or lower than the volume of the pores of the carrier;

(c) the pH of the suspension obtained according to (b) is brought to a level between 7 and 8.5;

(d) an aqueous solution, containing a soluble compound of Pd, is brought into contact with the suspension obtained according to (c), while keeping the pH constant within said 7-8.5 range, and the pH is then raised to a level equal to or higher than 12, according to known techniques; and (e) the thus obtained solid catalyst is recovered from the mother liquor by a conventional procedure.

6. A supported catalyst, prepared according to claim 5, containing from 0.1 to 5% b.w. of Pd, wherein Pd is distributed on the outer surface of a granule of low-ash carbon, the inner core of the granule being substantially void of Pd.

7. A catalyst according to claim 6, containing a liquid phase, consisting substantially of water and of said immiscible liquid hydrocarbon, the amount of liquid phase being at least 20% of the whole weight of the supported catalyst.

* * * * *